(12) United States Patent
Ferree

(10) Patent No.: US 6,344,058 B1
(45) Date of Patent: Feb. 5, 2002

(54) TREATING DEGENERATIVE DISC DISEASE THROUGH TRANSPLANTATION OF ALLOGRAFT DISC AND VERTEBRAL ENDPLATES

(76) Inventor: Bret A. Ferree, 1238 Cliff Laine Dr., Cincinnati, OH (US) 45208

(*) Notice: Subject to any disclaimer, the term of this patent is extended or adjusted under 35 U.S.C. 154(b) by 0 days.

(21) Appl. No.: 09/638,242

(22) Filed: Aug. 14, 2000

Related U.S. Application Data

(60) Provisional application No. 60/148,913, filed on Aug. 13, 1999.

(51) Int. Cl.$^7$ .................................................. A61F 2/44
(52) U.S. Cl. ..................................... 623/17.11; 128/898
(58) Field of Search ........................... 623/17.11–17.16, 623/11.11; 128/898

(56) References Cited

U.S. PATENT DOCUMENTS

| | | | |
|---|---|---|---|
| 5,258,043 A | * 11/1993 | Stone | 623/17.11 |
| 5,514,180 A | * 5/1996 | Heggeness et al. | 623/17.11 |
| 5,545,229 A | * 8/1996 | Parsons et al. | 623/17.11 |

OTHER PUBLICATIONS

Steven L. Frick et al.; "SPINE" 19(16): p1826–1835 1994.*
Orthopedics Today, Jul. 2000.
"Proceedings 13th Annual Meeting" North American Spine Society, Oct. 1998.
"Proceedings 14th Annual Meeting" North American Spine Society, Oct. 1999.

* cited by examiner

*Primary Examiner*—David H. Willse
*Assistant Examiner*—Suzette J. Jackson
(74) *Attorney, Agent, or Firm*—Gifford, Krass, Groh, Sprinkle, Anderson & Citkowski, PC

(57) ABSTRACT

The intervertebral disc and a portion of adjacent vertebrae obtained from recently deceased human or animal donors are used to restore disc function and eliminate pain in patients with disc disease. Cells harvested and cultured from the nucleus pulposus and/or the annulus fibrosis of a normal disc are added to the donor disc. Additional therapeutic substances like culture medium, growth factors, differentiation factors, hydrogels polymers, antibiotics, anti-inflammatory medications, or immunosuppressive medications may also be added to the transplanted disc unit.

22 Claims, No Drawings

TREATING DEGENERATIVE DISC DISEASE THROUGH TRANSPLANTATION OF ALLOGRAFT DISC AND VERTEBRAL ENDPLATES

REFERENCE TO RELATED APPLICATIONS

This application claims priority of U.S. provisional patent application Serial No. 60/148,913, filed Aug. 13, 1999, the entire contents of which are incorporated herein by reference.

FIELD OF THE INVENTION

This invention relates generally to the treatment of diseased or traumatized intervertebral discs, and more particularly, to the use of engineered disc tissues and endplate materials in conjunction with such treatment.

BACKGROUND OF THE INVENTION

Intervertebral discs provide mobility and a cushion between the vertebrae. At the center of each disc is the nucleus pulposus which, in the adult human, is composed of cells and an insoluble extracellular matrix which is produced by the nucleus itself. The extracellular matrix is composed of collagen, proteoglycans, water, and noncollagenous proteins.

The cells of the nucleus pulposus have chondrocyte-like features. Blood vessels do not course into the nucleus pulposus. Rather, the cells of the nucleus pulposus of the adult human obtain nutrients and eliminate waste by diffusion through blood vessels in the endplates of the vertebrae adjacent to the disc.

The nucleus pulposus is surrounded by the annulus fibrosis, which is composed of cells (fibrocyte-like and chondrocyte-like), collagen fibers, and non-fibrillar extracellular matrix. The components of the annulus are arranged in 15–25 lamellae around the nucleus pulposus.

To date, the treatment of degenerative disc disease has relied for the most part on eliminating the defective disc or disc function. This may be accomplished by fusing the vertebra on either side of the disc. In terms of replacement, most prior-art techniques use synthetic materials to replace the entire disc or a portion thereof. My pending U.S. patent application Ser. No. 09/415,382 discloses disc replacement methods and apparatus using synthetic materials.

Prosthetic disc devices replace nucleus pulposus and/or annulus fibrosis function. Nucleus replacing devices rely on the patient's annulus fibrosis to retain the device and perform annulus functions. Unfortunately, injuries to the annulus often accompany nucleus degeneration or trauma. In addition, the degenerated annulus fibrosis may produce pain in patients with nucleus replacement.

Devices that replace nucleus and annulus functions (total disc replacement) also exhibit certain weaknesses. Total disc replacements rely on attachment of the prosthetic disc to the vertebral endplates. Various methods of attachment have been described including the use of screws, spikes, and porous ingrowth material. The total disc/vertebral interface can loosen. The problems with prosthesis loosening and the revision surgery of the same are well known in prosthetic knee and hip surgery.

The future of treating degenerative disc disease therefore lies in treatments which preserve disc function. If disc function could be restored with biologic replacement or augmentation, the risk of premature wear out would be minimized, if not eliminated.

SUMMARY OF THE INVENTION

This invention resides in a method of treating a diseased or traumatized intervertebral disc located between adjacent vertebrae. According to the method, a disc unit is harvested from a recently deceased human or animal donor. As defined herein, this donor disc unit preferably includes not only an intervertebral disc having an extracellular matrix, but also a portion of the vertebrae on either side of the disc, including the endplates.

An affected disc is surgically removing from a patient, including the vertebral endplates and a portion of the vertebra on either side of the disc, thereby creating a void to be filled, and the donor disc unit is positioned within the surgically created void. The spine may be temporarily locally immobilized following placement of the donor disc unit into the surgically created void.

In the preferred embodiment, the donor disc unit is processed to kills living cells therewithin, while preserve the extracellular matrix. Nucleus pulposus and/or annulus fibrosis cells are harvested from a healthy intervertebral disc, cultured and transplanted into the donor disc unit. Precursors, or cells which differentiate into cells which provide nucleus pulposus and/or annulus fibrosis cell function may alternatively be used. The harvested cells are preferably kept viable until placed into the disc unit.

The method of the invention may further include the step of adding one or more therapeutic substances to the donor disc unit, the transplanted cells, or both prior to transplantation. Such therapeutic substances could include culture media, growth factors, differentiation factors, hydrogels, polymers, antibiotics, anti-inflammatory medications, immunosuppressive medications, or any useful combination thereof.

DETAILED DESCRIPTION OF THE INVENTION

Broadly according to this invention, a donor disc unit comprising an intervertebral disc and a portion of adjacent vertebrae, is obtained from a recently deceased human or animal donor, and used to restore disc function and eliminate pain in patients with degenerative disc disease. Autograft nucleus pulposus cells and annulus fibrosis cells are harvested from one or more healthy discs of a patient, preferably the same patient suffering from the disc disease, though any appropriate alternative source may be used, including fetal tissue or human sources, preferably having a familial relationship to minimize or avoid the need for immunosuppressive substances. The harvested cells are cultured then added to nucleus pulposus and annulus fibrosis extracellular matrix, preferably obtained from recently deceased humans or animals, and added to the donor disc unit.

The donor disc unit preferably includes a portion of vertebra on either side of the disc. Guidelines for tissue procurement including surgical technique of removal, number of hours between death of the donor and tissue procurement, and testing of the donor for infectious disease, are well described in open literature.

Following disc harvest, the tissue is processed to kill the living cells, though care is taken to preserve the extracellular matrix. Guidelines for processing the harvested disc as described are also well known to those skilled in the art. For example, such tissue may be frozen and thawed.

The disc being replaced, including the vertebral endplates and a portion of the vertebra on either side of the disc are removed from the affected patient. Surgical techniques to remove the disc and a portion of the vertebrae are well known to spine surgeons. The donor disc unit is then placed into the surgically created defect.

The replacement disc could be held in position with screws, plates, and/or rods attached between the donor bone and the host vertebrae. Although the plates or other rigid method of fixation may temporarily extend across the disc, such devices must ultimately removed, or not used at all, or else disc function would not be preserved. Preferably, then, synthetic or natural fibers are employed to extend across the disc space and attach to the host vertebrae. Appropriate fibers allow vertebral motion while helping to hold the grafted disc replacement in position.

If temporary local immobilization of the spine is necessary to assist bone growth form the host vertebrae to the donor vertebrae, surgically implanted pedicle screws and rods or plates may be used. The screws may be placed percutanously to allow easy removal after the vertebrae have healed. Alternatively, bio-resorbable screws may be used. Growth of the host vertebrae to the donor vertebrae may also be encouraged using growth factors such as bone morphogenetic proteins.

Cultured disc cells are added to the donor disc unit a few weeks or months following its transplantation. In the preferred embodiment, living disc cells are harvested from a normal disc of the patient with the degenerative disc disease. The living disc cells from the nucleus pulposus and annulus fibrosis are added to the donor nucleus and annulus respectively.

The delayed insertion of the cells would allow vascularization of the donor vertebrae prior to cell insertion. Vertebrae vascularization is important for diffusion to and from the transplanted disc cells. Alternatively, the cultured disc cells could be added to the donor disc before transplantation or at the time of transplantation. Culture media could be added to the disc with the transplanted cells.

Autologous nucleus pulposus chondrocyte- like cells may be obtained by aspiration or biopsy of healthy discs of the patient. The harvested nucleus pulposus cells are isolated and cultured using standard techniques. The harvested sterile nucleus pulposus is morselized and washed with phosphate buffered saline. The cells are released from the extracellular matrix with 0.2% clostridial collagenase (Worthington CLS II, 140 u/mg) and agitated. See Klagsbum, "Methods in Enzvmology, Vol. VII. The resulting suspension is filtered with a 153.mu.g nylon sieve (Tetko, Elmford, N.Y.).

The filtered solution is then centrifuged at 1800 rpm to remove the cells. The supernatant above the cells is removed with a micropipette until the cell concentration reaches $5.\text{times}.10.\text{sup}.7$ cells/cc. The harvested cells are grown in Hamm's F-12 culture media, 10% fetal calf serum, L-glutamine (292.mu.g/cc), penicillin (100 u/cc), streptomycin (100.mu.g/cc), and ascorbic acid (5.mu.g/cc) at 37.degrees C. The above method is described in detail in U.S. Pat. No. 6,060,053. The cells of the annulus fibrosis are harvested and cultured using similar techniques.

Precursor cells of nucleus pulposus cells or annulus fibrosis cells, chondrocytes, or other living cells that could function like nucleus pulposus cells or annulus fibrosis cells or that could differentiate into cells to build a functional nucleus pulposus or annulus fibrosis could also be used. The cultured cells are added to the donor disc through multiple small holes drilled through the annulus fibrosis into the nucleus pulposus.

Additional therapeutic substances could be added to the transplanted nucleus. For example, resorbable culture medium, tissue growth or differentiation factors (recombinant generated morphogenetic proteins, PDGF, TGF-β, EGF/TGF-α, IGF-I, βFGF), hydrogels, resorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. may be beneficial.

I claim:

1. A method of treating a diseased or traumatized intervertebral disc located between adjacent vertebrae, comprising the steps of:

harvesting a disc unit from a recently deceased human or animal donor, the donor disc unit including:
   an intervertebral disc having an extracellular matrix, and
   a portion of the vertebrae on either side of the disc, including the endplates;

surgically removing an affected disc from a patient, including the vertebral endplates and a portion of the vertebra on either side of the disc, thereby creating a void to be filled; and placing the donor disc unit into the surgically created void.

2. The method of claim 1, further including the step of processing the donor disc unit to kills living cells therewithin while preserve the extracellular matrix thereof.

3. The method of claim 1, further including the steps of:

harvesting cells from the nucleus pulposus, annulus fibrosis, or both the nucleus pulposus and annulus fibrosis of a healthy intervertebral disc;

culturing the cells; and transplanting the cells into the donor disc unit.

4. The method of claim 3, including the step of keeping the harvested cells viable until placed into the disc unit.

5. The method of claim 1, further including the step of temporarily immobilizing the spine following placement of the donor disc unit into the surgically created void.

6. The method of claim 1, further including the step of adding one or more therapeutic substances to the donor disc unit.

7. The method of claim 6, wherein the therapeutic substances include one or more of the following:

culture media, growth factors, differentiation factors, hydrogels, polymers, antibiotics, anti-inflammatory medications, or immunosuppressive medications.

8. A method of treating a diseased or traumatized intervertebral disc located between adjacent vertebrae, comprising the steps of:

harvesting:
   a) cells that differentiate into nucleus pulposus like cells, or live cells that function like cells of the nucleus pulposus,
   b) cells that differentiate into annulus fibrosis like cells, or live cells that function like cells of the annulus fibrosis, or
   a) and b);

harvesting a disc unit from a recently deceased human or animal donor, the donor disc unit including:
   an intervertebral disc having an extracellular matrix, and
   a portion of the vertebrae on either side of the disc, including the endplates;

combining the harvested cells with disc unit; and transplanting the disc unit into the disc being treated.

9. The method of claim 8, further including the step of adding one or more therapeutic substances to the engineered nucleus pulposus.

10. The method of claim 9, wherein the therapeutic substances include one or more of the following:
    culture media, growth factors, differentiation factors, hydrogels, polymers, antibiotics, anti-inflammatory medications, or immunosuppressive medications.

11. The method of claim 8, further including the step of keeping the harvested cells viable until placed into the disc unit.

12. A method of preparing a donor intervertebral disc unit, comprising the steps of:
    harvesting a disc unit from a recently deceased human or animal donor, the donor disc unit including:
        an intervertebral disc having an extracellular matrix, and
        a portion of the vertebrae on either side of the disc, including the endplates; and
    keeping the harvested disc unit viable until transplantation.

13. A donor disc unit prepared according to the method of claim 12.

14. The donor disc unit of claim 13, wherein living cells are killed to preserve the extracellular matrix.

15. The method of claim 12, further including the steps of:
    harvesting cells from the nucleus pulposus, annulus fibrosis, or both the nucleus pulposus and annulus fibrosis of a healthy intervertebral disc;
    culturing the cells; and
    transplanting the cells into the donor disc unit.

16. A donor disc unit prepared according to the method of claim 15.

17. The donor disc unit of claim 16, further including one or more therapeutic substances.

18. The donor disc unit of claim 17, wherein the therapeutic substances include one or more of the following:
    culture media, growth factors, differentiation factors, hydrogels, polymers, antibiotics, anti-inflammatory medications, or immunosuppressive medications.

19. A method of preparing a donor intervertebral disc unit, comprising the steps of:
    harvesting:
        a) cells that differentiate into nucleus pulposus like cells, or live cells that function like cells of the nucleus pulposus,
        b) cells that differentiate into annulus fibrosis like cells, or live cells that function like cells of the annulus fibrosis, or
        a) and b);
    harvesting a disc unit from a recently deceased human or animal donor, the donor disc unit including:
        an intervertebral disc having an extracellular matrix, and
        a portion of the vertebrae on either side of the disc, including the endplates;
    combining the harvested cells with disc unit; and
    keeping the disc unit viable until transplantation.

20. A donor disc unit prepared according to the method of claim 19.

21. The donor disc unit of claim 20, wherein the engineered nucleus pulposus includes one or more therapeutic substances.

22. The donor disc unit of claim 21, wherein the therapeutic substances include one or more of the following:
    culture media, growth factors, differentiation factors, hydrogels, polymers, antibiotics, anti-inflammatory medications, or immunosuppressive medications.

* * * * *